(12) United States Patent
Flock (10) Patent No.: US 9,217,717 B2
(45) Date of Patent: Dec. 22, 2015

(54) TWO DIMENSIONAL OPTICAL DETECTOR WITH MULTIPLE SHIFT REGISTERS

(71) Applicant: KLA-Tencor Corporation, Milpitas, CA (US)

(72) Inventor: Klaus Flock, Sunnyvale, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 188 days.

(21) Appl. No.: 14/103,635

(22) Filed: Dec. 11, 2013

(65) Prior Publication Data

US 2014/0166862 A1 Jun. 19, 2014

Related U.S. Application Data (60) Provisional application No. 61/738,348, filed on Dec. 17, 2012.

(51) Int. Cl.
*G01N 21/95* (2006.01)

(52) U.S. Cl.
CPC .................................. *G01N 21/9501* (2013.01)

(58) Field of Classification Search
CPC ................................................. G01N 21/9501
USPC ........................................ 250/208.2; 348/280
See application file for complete search history.

(56) References Cited

U.S. PATENT DOCUMENTS

| | | | |
|---|---|---|---|
| 4,851,914 A * | 7/1989 | Pfanhouser et al. | 348/217.1 |
| 5,055,667 A * | 10/1991 | Sayag | 250/208.1 |
| 5,900,949 A | 5/1999 | Sampas | |
| 2002/0097330 A1 | 7/2002 | Spears et al. | |
| 2002/0135689 A1 * | 9/2002 | Uya | 348/280 |
| 2003/0025822 A1 * | 2/2003 | Shimada | 348/370 |
| 2004/0090626 A1 | 5/2004 | Wielsch et al. | |
| 2004/0189836 A1 * | 9/2004 | Spears et al. | 348/241 |
| 2005/0056771 A1 | 3/2005 | Atlas et al. | |
| 2006/0082670 A1 | 4/2006 | Parks | |

OTHER PUBLICATIONS

International Search Report and Written Opinion mailed on Apr. 28, 2014, for PCT Application No. PCT/US2013/075836 filed on Dec. 17, 2013, by KLA-Tencor Corporation, 13 pages.

* cited by examiner

*Primary Examiner* — Seung C Sohn
(74) *Attorney, Agent, or Firm* — Spano Law Group; Joseph S. Spano (57) ABSTRACT

Methods and systems for enhancing the throughput of a metrology system generating measurement signals based on at least two different optical properties of the illumination light are presented. A detector having a two dimensional photosensitive area is subdivided into multiple photosensitive stripes by multiple, independent linear arrays of shift register elements located within the photosensitive area. Charge transfer from pixels within each stripe is directed to a distinct linear array of shift register elements. Each photosensitive stripe is able to resolve an optical property dispersed across the length of each stripe with relatively high resolution. In addition, the detector is able to resolve another optical property dispersed across several photosensitive stripes in a direction orthogonal to each linear array of shift registers at a relatively low resolution.

20 Claims, 8 Drawing Sheets

TWO DIMENSIONAL OPTICAL DETECTOR WITH MULTIPLE SHIFT REGISTERS

CROSS REFERENCE TO RELATED APPLICATION

The present application for patent claims priority under 35 U.S.C. §119 from U.S. provisional patent application Ser. No. 61/738,348, entitled "Multiple Horizontal Shift-Registers for Optical 2D-Detection," filed Dec. 17, 2013, the subject matter of which is incorporated herein by reference.

TECHNICAL FIELD

The described embodiments relate to systems for surface inspection, and more particularly to semiconductor wafer inspection modalities.

BACKGROUND INFORMATION

Semiconductor devices such as logic and memory devices are typically fabricated by a sequence of processing steps applied to a substrate or wafer. The various features and multiple structural levels of the semiconductor devices are formed by these processing steps. For example, lithography among others is one semiconductor fabrication process that involves generating a pattern on a semiconductor wafer. Additional examples of semiconductor fabrication processes include, but are not limited to, chemical-mechanical polishing, etching, deposition, and ion implantation. Multiple semiconductor devices may be fabricated on a single semiconductor wafer and then separated into individual semiconductor devices.

Measurement processes are used at various steps during a semiconductor manufacturing process to detect defects on wafers to promote higher yield. As design rules and process windows continue to shrink in size, metrology systems are required to capture a wider range of physical defects on wafer surfaces while maintaining high throughput.

Modern, complex optical metrology systems are characterized by multiple sets of system parameters such as a range of polar angles of incidence (AOI), a range of azimuth angles of incidence, a range of illumination wavelengths, a range of polarization states, a range of diffraction orders, etc.

Traditionally, measurement data is collected over the full range of each of these multiple sets of system parameters to maximize the amount of measurement data available for analysis to meet the semiconductor device metrology challenge. Often, a significant portion of the data acquisition is performed sequentially. However, this approach to data collection and analysis is often prohibitively time consuming.

In one example, it is contemplated that a two dimensional detector (e.g., a charge coupled device camera) is employed to resolve two beam properties. State of the art two dimensional detectors (e.g., back-thinned CCD detectors) allow for a two dimensional readout of the active area by shifting pixels vertically to a shift register at the bottom of the active area, followed by reading out each pixel of the shift register. This mode reads one row at a time and requires M×N clock cycles to read the active area, where M is the number of columns of pixels and N is the number of rows of pixels. In one example, each column of pixels extends in a vertical direction and each row of pixels extends in a horizontal direction. This mode takes on the order of 100 to 200 milliseconds for an array of 1024×38 pixels. This results in an intolerably slow mode of operation. In addition, if the detector is exposed to light during readout, this leads to mixing of information for a signal dispersed across a number of rows of pixels.

Accordingly, in a conventional spectroscopic system, where charges are being accumulated continuously, one may resolve a spectrum along the vertical dimension, but not without introducing some systematic error and/or giving up a significant amount of useful photon flux. In one example, different angles of incidence (AOI) are dispersed along the vertical direction. Information accumulated from one portion of the pupil at a given row is mixed with the information from an adjacent portion of the pupil for each vertical shift. This process repeats for all rows of exposed pixels. The beam could be shuttered during the reading of the CCD. However, conventional shutters have too much inertia to follow at a rate that corresponds to integration times on the order of two milliseconds. As a result, throughput would suffer.

In another example, a two dimensional CCD is operated in a vertically binned mode. The charges from all rows are first transferred to a shift register at the bottom of the active area. Subsequently, the shift register is clocked out once for the given number of pixels in the longitudinal direction. Such an operation takes M+N clock cycles, and thus is significantly faster than a full 2D-readout (i.e., M×N). However, the resolution in the vertical dimension is lost. Thus, vertical binning is a one dimensional mode of operation for a two dimensional detector.

Improvements to the dynamic range and throughput of array based detectors employed in optical metrology systems are desired to detect a comprehensive set of information from the specimen, including, but not limited to, surface and substrate (bulk) properties, defects, film thicknesses, critical dimensions (CD), composition (n & k), anisotropy, scattered light/surface roughness, edge roughness, etc., on a wafer with greater sensitivity using multiple sets of system parameters at sufficiently high throughput.

SUMMARY

Methods and systems for enhancing the throughput of a metrology system generating measurement signals based on at least two different optical properties of the illumination light are presented. A detector having a two dimensional photosensitive area is subdivided into multiple photosensitive stripes by multiple, independent linear arrays of shift register elements located within the photosensitive area. Charge transfer from pixels within each stripe is directed to a distinct linear array of shift register elements. Each photosensitive stripe is able to resolve an optical property dispersed across the length of each stripe with relatively high resolution. In addition, the detector is able to resolve another optical property dispersed across several photosensitive stripes in a direction orthogonal to each linear array of shift registers at a relatively low resolution.

In general, the photodetector elements may be any suitable size, and each array of photodetector elements may include any suitable number of row and column elements. However, to maintain high throughput within a metrology system, the number of photosensitive elements aligned with the high resolution direction should be significantly larger than the number of photosensitive elements aligned with the low resolution direction. For example, in some embodiments, the number of photosensitive elements aligned with the high resolution direction should be ten times larger than the number of photosensitive elements aligned with the low resolution direction. In some embodiments, the number of photosensitive elements aligned with the high resolution direction should be one hundred times larger than the number of photosensitive elements aligned with the low resolution direction. In some embodiments, the number of photosensitive elements aligned with the high resolution direction should be one thousand times larger than the number of photosensitive elements aligned with the low resolution direction.

Similarly, in general, the number of independent arrays of photodetector elements within the photosensitive area may be any suitable number. However, to maintain high throughput within a metrology system, the number of independent arrays of photodetector elements within the sensitive area should be significantly less than the number of photosensitive elements aligned with the high resolution direction. In some examples, the number of independent arrays of photodetector elements within the photosensitive area is three or more, but less than twenty five. In some examples, the number of independent arrays of photodetector elements is three or more, but less than ten.

Because the arrays of shift registers are located within the photosensitive area, it is preferable to take measures to avoid contaminating signals in the shift registers by limiting the exposure of each array of shift registers in the photosensitive area to incoming radiation.

In some embodiments, an adequate layer of opaque material is located over each shift register array in the path of incoming radiation to limit exposure. In some embodiments, an optical shield is located over shift registers located in the photosensitive area 160 to prevent accumulation of charge in the shift registers due to exposure. In some other embodiments, the accumulation of charge at each shift register array is mitigated by shuttering the illumination of the detector during read-out. In this manner, shift registers may be read-out while preventing exposure of the detector to incoming light which would otherwise contaminate the signals read out from unshielded shift registers.

Many different optical shuttering mechanisms may be contemplated. By way of non-limiting example, any of a tuning fork chopper, an Accousto Optical Tunable Filter (AOTF), an Electro Optical Switch (EOS), and a mechanical shutter may be located in an optical path of the collected light and controlled to selectively block or redirect light from reaching unshielded shift registers during read-out.

In another example, the radiation source itself may be controlled to suspend light generation or redirect generated light to prevent illumination of unshielded shift registers during read-out.

In some embodiments, the detector is arranged in a multi-tap configuration to increase horizontal read-out speed with a minimum of added complexity.

In some embodiments, the detector includes a center divider to divide the photosensitive area in such a way as to provide a double width of photodetectors within the photosensitive area that is not subject to obfuscation due to the presence of an array of shift registers.

In some embodiments, the photodetector elements are are rectangular in shape to increase read-out speed.

The foregoing is a summary and thus contains, by necessity, simplifications, generalizations and omissions of detail; consequently, those skilled in the art will appreciate that the summary is illustrative only and is not limiting in any way. Other aspects, inventive features, and advantages of the devices and/or processes described herein will become apparent in the non-limiting detailed description set forth herein.

DETAILED DESCRIPTION

Reference will now be made in detail to background examples and some embodiments of the invention, examples of which are illustrated in the accompanying drawings.

A detector having a two dimensional photosensitive area subdivided by multiple, independent linear arrays of shift register elements located within the photosensitive area is described herein. The photosensitive area is subdivided by the linear arrays of shift registers into multiple photosensitive stripes each having a relatively high resolution in a direction aligned with each linear array of shift registers and a relatively low resolution in a direction orthogonal to each linear array of shift registers. Charge transfer from pixels within each stripe is directed to a distinct linear array of shift register elements.

The number of stripes is relatively small compared to the number of pixels in each stripe that are aligned with each linear array of shift registers. In this manner, the detector is able to resolve an optical property dispersed across the length of each stripe with relatively high resolution, and resolve another optical property dispersed across several different stripes with relatively low resolution. In one example, the wavelength of collected light is dispersed along the length of each stripe and is resolved at high resolution (e.g., 1024 pixels), while collected light associated with different angles of incidence is dispersed across several different stripes and is resolved at low resolution (e.g., five different stripes). In an analogous manner, arbitrary combinations of beam properties, such as AOI, azimuth, wavelength, and polarization may be simultaneously resolved at two different resolutions with a single two dimensional detector.

The detector offers unique advantages for optical metrology. In some applications the resolution requirements for two different optical properties are quite different. One may desire to resolve, for instance, 1024 different wavelengths, but only a small number of angles of incidence (AOI). The detector described herein is able to resolve beam properties in two dimensions with relatively large differences in resolution requirements for each orthogonal dimension, and do so at high-speed. In addition, the full system NA is carried to the detector. This ensures an optimal spot-size for diffraction limited imaging systems.

In one example, a metrology system is configured to simultaneously detect the response of a specimen to illumination light over ranges of at least two different illumination parameters in accordance with the novel detection systems and methods described herein.

Figure 1:
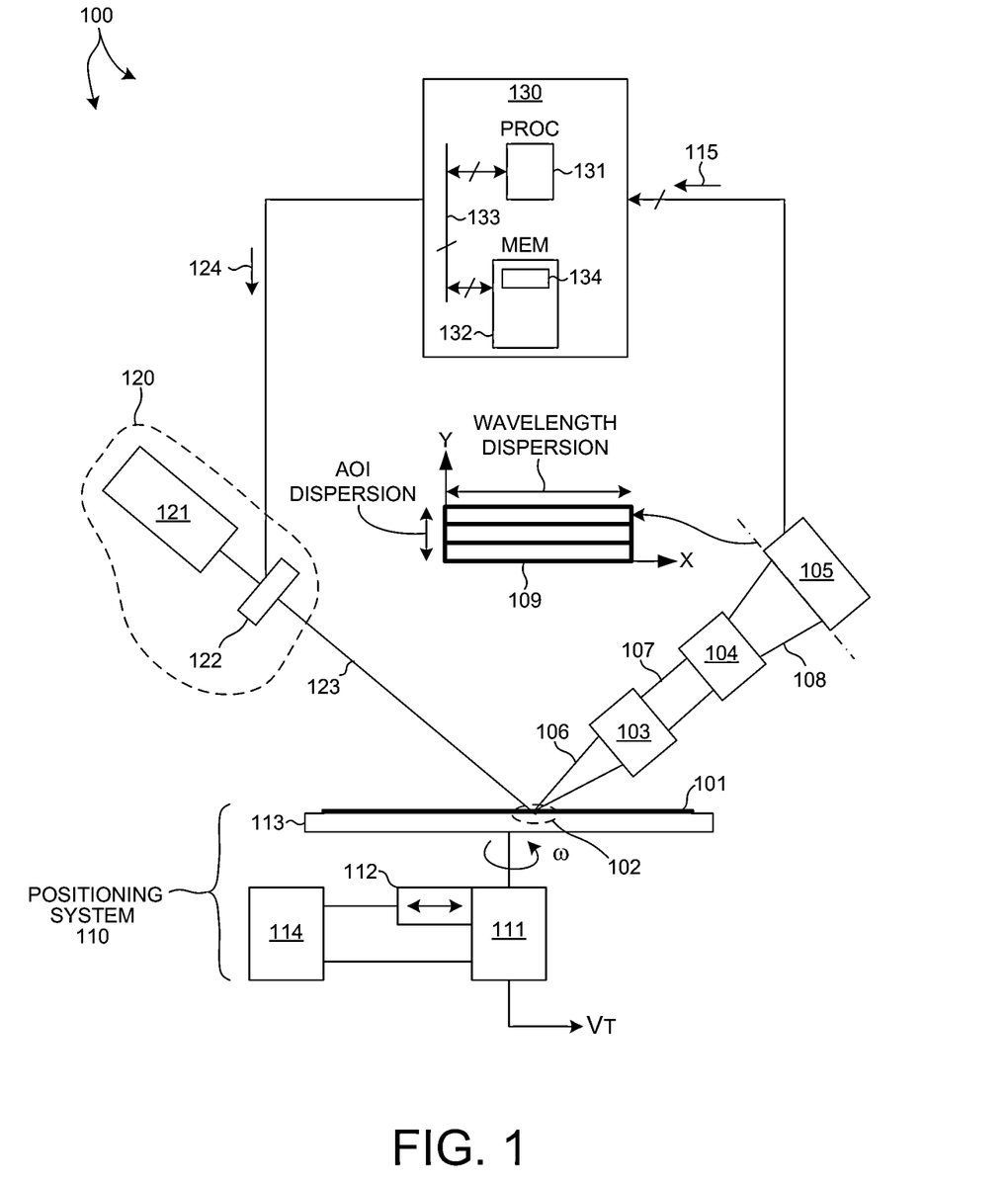
FIG. 1 is a simplified diagram illustrative of one embodiment of a metrology system 100 for simultaneous detection of the response of a specimen to illumination light over ranges of at least two different illumination parameters.

FIG. 1 depicts a metrology system 100 for simultaneous detection of the response of a specimen to illumination light over ranges of at least two different illumination parameters in one embodiment. As depicted in FIG. 1, metrology system 100 may be used to perform optical scatterometry measurements over a measurement box area 102 of a specimen 101 disposed on a specimen positioning system 110. In general, metrology system 100 is configured to simultaneously illuminate specimen 101 with illumination light over ranges of at least two different illumination parameters. By way of non-limiting example, the illumination parameters are any of illumination wavelength, angle of incidence, azimuth angle, polarization state, etc.

As depicted in FIG. 1, metrology system 100 is configured to illuminate specimen 101 with illumination light over a range of illumination wavelengths and a range of AOIs. Metrology system 100 includes an optical illumination system 120 including an optical illumination source 121 and illumination optics 122 configured to shape and direct incident optical illumination beam 123 from optical illumination source 121 to the measurement box 102 of specimen 101. By way of non-limiting example, optical illumination source 121 includes one or more arc lamps, lasers, light emitting diodes, laser driven plasma sources, and laser driven supercontinuum sources, or any combination thereof. In general, any suitable optical illumination source may be contemplated. In some embodiments, optical illumination source 121 is configured to generate illumination light having wavelength components between 100 nanometers and 2000 nanometers.

Illumination optics 122 is configured to collimate or focus incident optical illumination beam 123 to measurement box 102 of specimen 101. In some embodiments, illumination optics 122 includes one or more optical mirrors, focusing or defocusing optics, optical waveplates, optical apertures, optical monochromators, and optical beam stops, or any combination thereof.

Metrology system 100 is further configured to collect light 106 that emanates from the specimen 101 in response to the illumination light 123. In the depicted example, light at different wavelengths and AOIs emanating from specimen 101 is simultaneously collected by collection optics 103. By way of non-limiting example, collection optics 103 includes collection mirrors for focusing collected light onto dispersion optics 104 and detector 105.

Metrology system 100 is further configured to spatially separate the collected light in one direction (e.g., x-direction) according to values of one illumination parameter (e.g., wavelength) and spatially separate the collected light in another direction (e.g., y-direction) according to values of another illumination parameter (e.g., AOI). The spatially separated light is projected onto the surface 109 of detector 105. In this manner, two different spatially resolved illumination parameters are simultaneously provided to the detector of the metrology system.

In general, any suitable mechanism to map wavelength and AOI onto two different directions in a plane may be incorporated into metrology system 100. For example, metrology system 100 may include optics with different optical power (e.g., cylindrical power, toroidal power, etc.) in two different directions to map wavelength and AOI across two different directions on the detection plane 109 of 2D detector 105. In this manner, dispersion optics 104 and detector 105 provide a 2D spectrometer function having one axis for AOI and another axis for wavelength.

Figure 2:
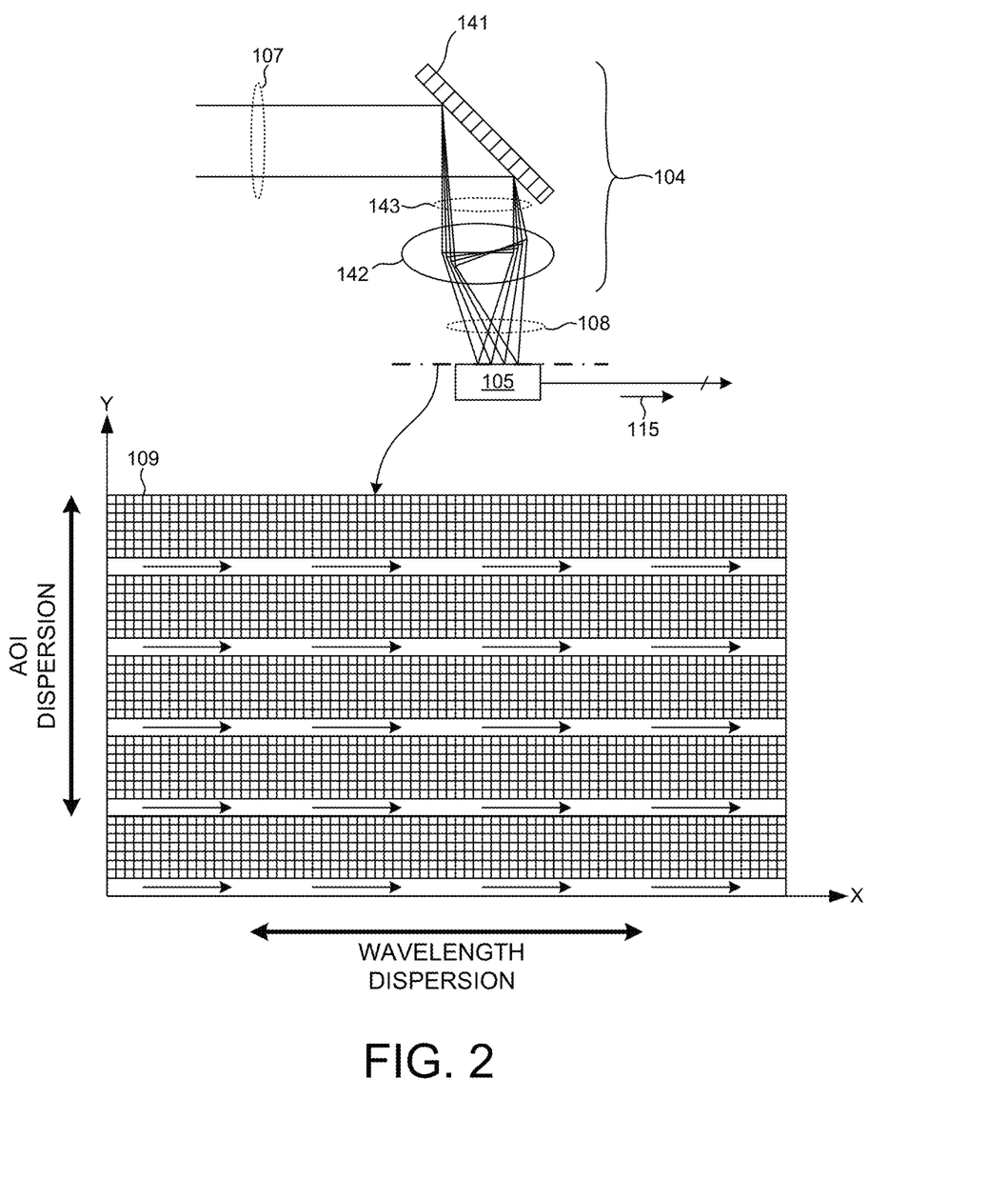
FIG. 2 is a simplified diagram illustrative of dispersion optics 104 of metrology system 100 in one embodiment.

By way of non-limiting example, dispersion optics 104, illustrated in FIG. 2, includes a diffraction element (e.g., diffraction grating) that receives collected light 107 and spatially separates collected light 107 across the surface 109 of detector 105 in one direction (e.g., x-direction) according to wavelength. Dispersion optics 104 also includes a cylindrical lens 142 that receives diffracted light 143 and spatially separates collected light 107 across the surface 109 of detector 105 in another direction (e.g., y-direction) according to AOI. In a specific implementation the dispersive element includes a cylinder that is configured to turn a point focus into a line which is proportional in length to the numerical aperture (NA), which is in turn related to the collected AOI. In this manner, spatially separated light 108 projected onto the surface 109 of detector 105 is mapped as a function of wavelength to a first axis (e.g., x-direction) and as a function of AOI in a second axis (e.g., y-direction). Dispersion optics 104 may be configured to have power in the wavelength direction that causes the detector 105 to be at or near a plane conjugate with the field stop and have power in the AOI direction to make the detector plane to be at or near conjugate to the pupil plane. In general, any two different optical parameters may be spatially separated in two different directions across the detecting plane 109 of detector 105.

Metrology system 100 is further configured to simultaneously detect collected light having two different optical properties spatially separated in two different directions across the detector surface. Optical detector 105 collects optical radiation 108 scattered from specimen 101 and generates an output signal 115 indicative of properties of specimen 101 that are sensitive to the incident optical radiation 123. In some embodiments, scattered optical radiation 108 is collected by optical detector 105 while specimen positioning system 110 locates and orients specimen 101. The optical detector 105 is able to resolve one or more optical photon energies and produces signals for each optical energy component indicative of properties of the specimen.

In one novel aspect, detector 105 includes multiple, independent arrays of shift registers located in the photosensitive area that subdivide the photosensitive area into several independent photosensitive regions. Each photosensitive region includes an array of photodetectors with charge transfer to an associated array of shift registers.

Figure 3:
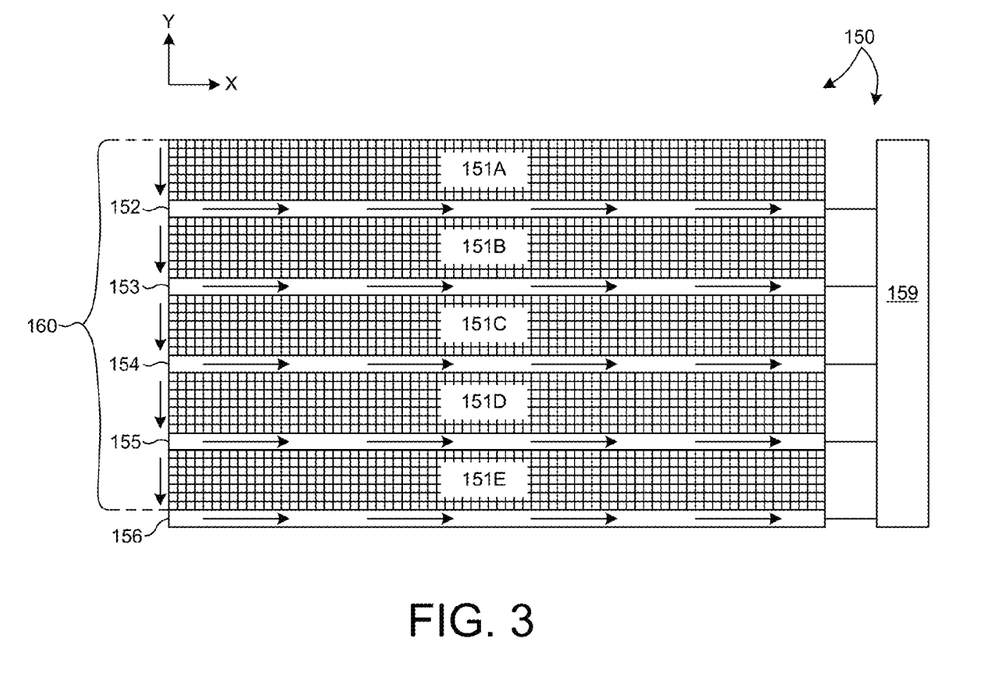
FIG. 3 is a simplified diagram illustrative of an embodiment 150 of a detector described with reference to metrology system 100.
Figure 6:
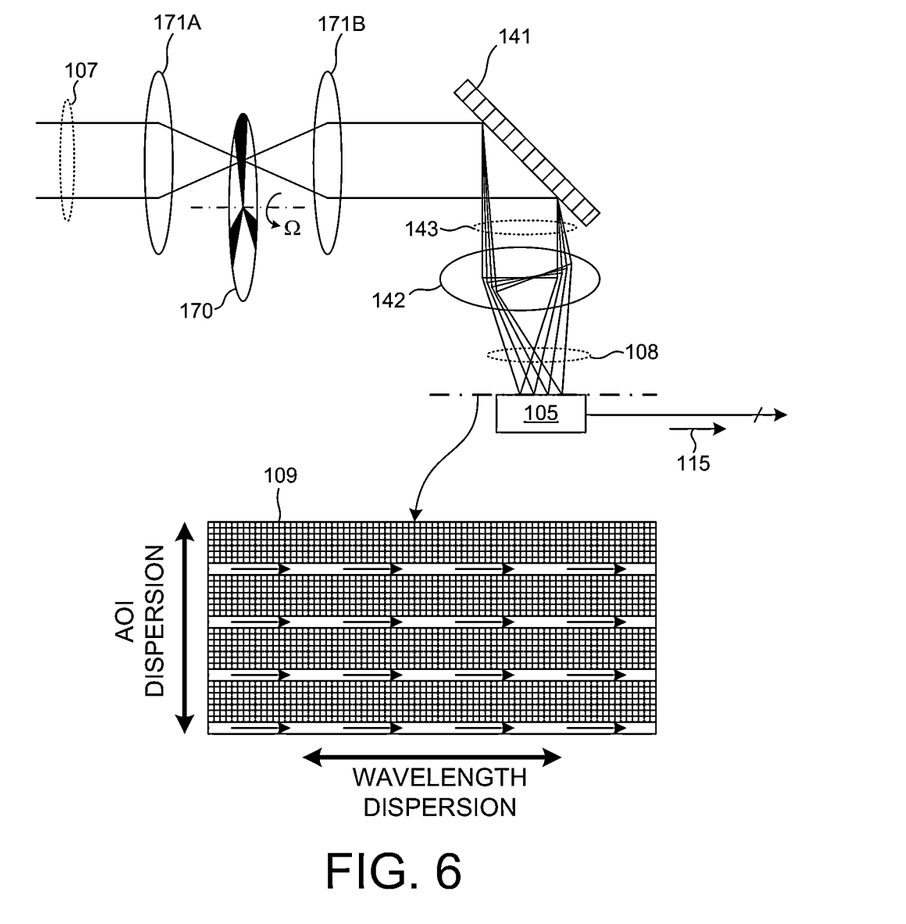
FIG. 6 is a simplified diagram illustrative of an external chopper wheel 170 located in the optical path of collected light 107 described with reference to metrology system 100.

FIG. 3 is a diagram illustrative of an embodiment 150 of detector 105 described with reference to FIGS. 1, 2 and 6. Detector 150 includes a photosensitive area 160 that is subdivided into multiple, independent arrays of photodetector elements 151A-151E by independent arrays of shift registers 152-155, respectively. As depicted in FIG. 3, charge accumulated within elements of photodetector array 151A is shifted downward to shift register array 152, and then read out of shift register array 152 by read-out electronics 159. Similarly, charges accumulated within elements of photodetector arrays 151B-151E are shifted downward to shift register arrays 153-156, respectively, and then are read out of the respective shift register arrays by read-out electronics 159.

As depicted in FIG. 3, each array of photodetector elements includes a relatively large number of photodetector elements in one direction (i.e., x-direction) and a relatively small number of photodetector elements in another, orthogonal direction (i.e., y-direction). Similarly, the number of shift-register arrays is also relatively small.

In general, the photodetector elements may be any suitable size, and each array of photodetector elements may include any suitable number of row and column elements. However, to maintain high throughput within a metrology system (e.g., metrology system 100), the number of photosensitive elements aligned with the high resolution direction should be significantly larger than the number of photosensitive elements aligned with the low resolution direction. For example, in some embodiments, the number of photosensitive elements aligned with the high resolution direction should be ten times larger than the number of photosensitive elements aligned with the low resolution direction. In some embodiments, the number of photosensitive elements aligned with the high resolution direction should be one hundred times larger than the number of photosensitive elements aligned with the low resolution direction. In some embodiments, the number of photosensitive elements aligned with the high resolution direction should be one thousand times larger than the number of photosensitive elements aligned with the low resolution direction.

Similarly, in general, the number of independent arrays of photodetector elements within the photosensitive area may be any suitable number. However, to maintain high throughput within a metrology system (e.g., metrology system 100), the number of independent arrays of photodetector elements within the sensitive area should be significantly less than the number of photosensitive elements aligned with the high resolution direction. In some examples, the number of independent arrays of photodetector elements within the photosensitive area is three or more, but less than twenty five. In some examples, the number of independent arrays of photodetector elements is three or more, but less than ten.

In one embodiment, each photodetector element is 24 micrometers by 24 micrometers, each array of photodetector elements includes 1024 elements in the x-direction and 10 elements in the y-direction, and there are five independent arrays of photodetector elements within the photosensitive area. A shift register array is located between each array of photodetector elements, hence there are five independent shift register arrays. Charge accumulated in each array of photodetector elements is transferred to an adjacent, associated shift register array.

In some examples, read-out is triggered independently for each array of photodetectors and associated shift register. In some other examples, read-out is performed in a parallel mode, where all of the arrays of photodetectors, each with its associated shift register, are being read out in parallel.

In some examples, charge transfer from an array of photodetectors to its associated shift-register (i.e., charge transfer in the y-direction as illustrated in FIG. 3) involves an entire row of photodetector elements in the photodetector array (i.e., all photodetector elements in a row aligned with the x-direction as illustrated in FIG. 3). In this example of vertical binning, charge associated with each row is sequentially transferred to the shift register array at each clock cycle, and then the shift register array is read out one column at a time.

However, in general, charge transfer from photodetectors in each photodetector array to its associated shift register may be performed in any suitable order or grouping.

In some examples, charge transfer from an array of photodetectors to its associated shift register involves more than one row of photodetector elements in the photodetector array. In one example, charge associated with all rows of photodetector elements in the photodetector array are transferred to the associated shift register array in one clock cycle. Subsequently, each shift register element in the array is read out sequentially by read out electronics 159. In this mode of operation each photodetector array operates as a one dimensional detector, but the independence of each spatially separated photodetector array provides limited resolution in the y-direction in this mode of operation. In general, any number of rows of photodetector elements in a photodetector array may be read out together to achieve a desired resolution in the y-direction.

In some embodiments, readout electronics are constructed on the same substrate as the detectors described herein to reduce cost and improve data processing speed.

In some embodiments, the photodetector elements of detector 150 are photodiodes, such as a photodiode array model number S11151 manufactured by Hamamatsu, Photonics K.K. (Japan). Photodiode elements may be operated in a front illumination mode and maintain sensitivity to UV radiation (e.g., 170-850 nanometers) in the photosensitive area. In some other embodiments, the photodetector elements of detector 150 are charge coupled devices (CCDs), such as a CCD array model number S11963 manufactured by Hamamatsu, Photonics K.K. (Japan). CCD elements must be operated in a back illumination mode through a back-thinned area of the CCD device to maintain sensitivity to UV radiation (e.g., 170-850 nanometers) in the photosensitive area. In general, detector 150 may include a suitable arrangement of CCD elements, photodiode elements, CMOS elements, and photomultiplier tube elements.

Figure 4:
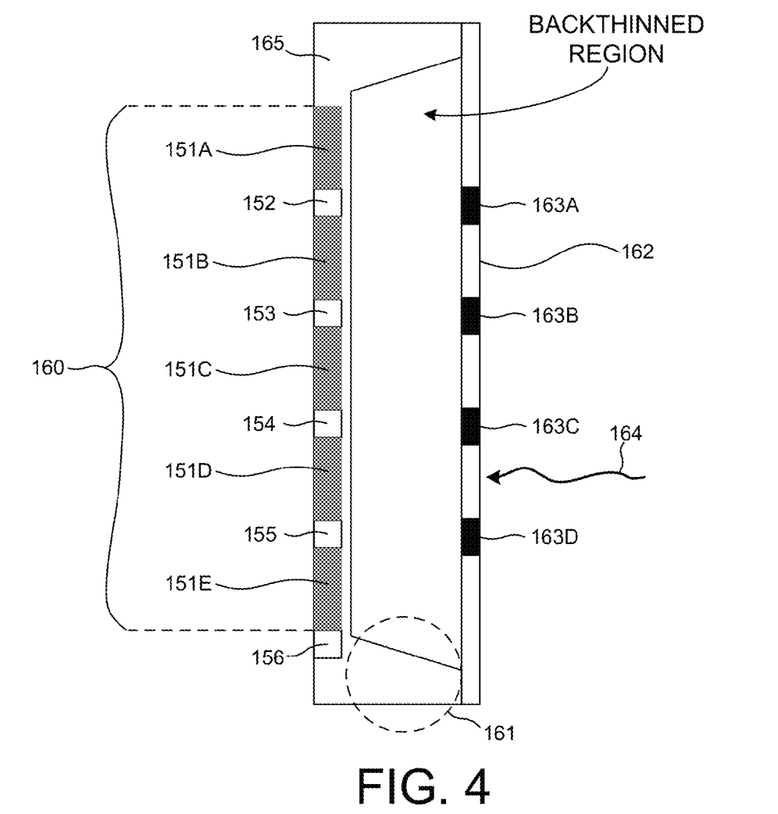
FIG. 4 is a simplified diagram illustrative of a cross-sectional view of detector 150 described with reference to FIG. 3.

FIG. 4 is a diagram illustrative of a cross-sectional view of detector 150 described with reference to FIG. 3. As depicted in FIG. 4, detector 150 is a single semiconductor device constructed, by way of non-limiting example, from a single piece of silicon 165. In the depicted example, the photosensitive area 160 includes multiple, independent arrays 151A-151E of CCD elements each separated by an independent array of shift registers located in the photosensitive area 160. As depicted in FIG. 4, the photosensitive area 160 of detector 150 is back-thinned to allow incoming photons 164 to reach the photodetector elements without excessive absorption losses.

Because the arrays of shift registers 152-155 are located within the photosensitive area 160, it is preferable to take measures that avoid contaminating the signals in the shift registers by limiting the exposure of each array of shift registers in the photosensitive area to incoming radiation (e.g., photons 164).

In some embodiments, an adequate layer of opaque material is located over each shift register array in the path of incoming radiation to limit exposure. In some examples, a lithographic and etch process leaves a sufficient amount of silicon directly over each shift register array. In one example, silicon back-thinning is limited to areas associated with each photodetector array. For example, as illustrated in FIG. 4, an amount of silicon 161 remains behind after back-thinning and this amount of silicon prevents significant incoming radiation from reaching shift register array 156. This approach has been shown to be effective in protecting shift registers located at the periphery of a photosensitive area.

Figure 5:
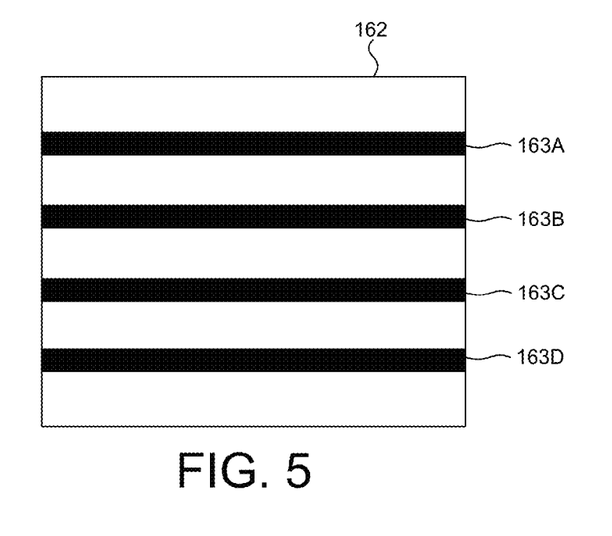
FIG. 5 is a simplified diagram illustrative of an optical shield 162 in one embodiment.

In some examples, an optical shield 162 is located over shift registers located in the photosensitive area 160 to prevent accumulation of charge in the shift registers due to exposure. As illustrated in FIG. 4, optical shield 162 includes opaque patterns 163A-D that effectively shadow shift register arrays 152-155 and prevent excessive exposure to incoming radiation 164. FIG. 5 illustrates a top view of optical shield 162 illustrating opaque patterns 163A-D as stripes of opaque material that are aligned with each respective shift register array. In one example, optical shield 162 is constructed from sapphire material printed with a pattern of opaque material such as a metal (e.g., aluminum, copper, gold, silver, etc.) or a non-metallic, opaque material.

As illustrated in FIG. 4, optical shield 162 may be spaced apart from the photosensitive region, for example, also acting as an external cover glass for the detector. The patterned mask could, for example, be placed on the inside of a detector window. In general, it may be advantageous to locate optical shield 162 as close as practically possible to the shift register arrays.

The size of each opaque pattern is determined to shadow each respective shift register array as precisely as possible. Each opaque pattern stripe could be wider or narrower than the associated shift registers. For example if incoming light is converging, the stripes may be wider. Conversely, if the incoming light is diverging the stripes may be narrower, so that the shadow cast over the corresponding shift register sufficiently covers the shift register without excessively blocking light incident to adjacent photodetectors. Similarly, diffraction effects may also dictate that the stripes be wider than the shift registers to sufficiently shadow the corresponding shift register. This may be particularly important as the distance between the photosensitive area and optical shield 162 increases.

In some other embodiments, the accumulation of charge at each shift register array is mitigated by shuttering of the illumination of the detector during read-out. In this manner, shift registers may be read-out while preventing exposure of the detector to incoming light which would otherwise contaminate the signals read out from unshielded shift registers. Many different optical shuttering mechanisms may be contemplated. By way of non-limiting example, any of a tuning fork chopper, an Accousto Optical Tunable Filter (AOTF), an Electro Optical Switch (EOS), and a mechanical shutter may be located in an optical path of the collected light and controlled to selectively block or redirect light from reaching unshielded shift registers during read-out. In another example, the radiation source itself may be controlled to suspend light generation or redirect generated light to prevent illumination of unshielded shift registers during read-out.

In one non-limiting example, the rotation of an external chopper wheel may be synchronized with the read-out timing to effectively limit the exposure of shift registers in the photosensitive area to incoming radiation. FIG. 6 is a diagram illustrative of an external chopper wheel 170 located in the optical path of the collected light 107. As illustrated in FIG. 6, chopper wheel 170 is located in a focal plane of collected light 107 generated by optical elements 171A and 171B. In general, chopper wheel 170 may be located anywhere in the optical path of metrology system 100, and traverse the optical path in any desired direction. However, it may be advantageous to locate chopper wheel 170 in a focal plane to alternately block and transmit light as sharply as possible (i.e., with a minimum of transition time).

Chopper wheel 170 includes transmissive and opaque regions of material that are alternately passed through the optical path in accordance with the rotational speed, $\Omega$, of the chopper wheel itself. In one example, a photo-sensor detects the point in time when an opaque region of the chopper wheel 170 traverses the optical path. In response, a synchronization circuit (not shown) triggers the read-out of the shift registers while the opaque region of the chopper wheel 170 is traversing the beam path. Read-out of the shift registers may be conducted in a parallel or sequential mode as desired.

Figure 7:
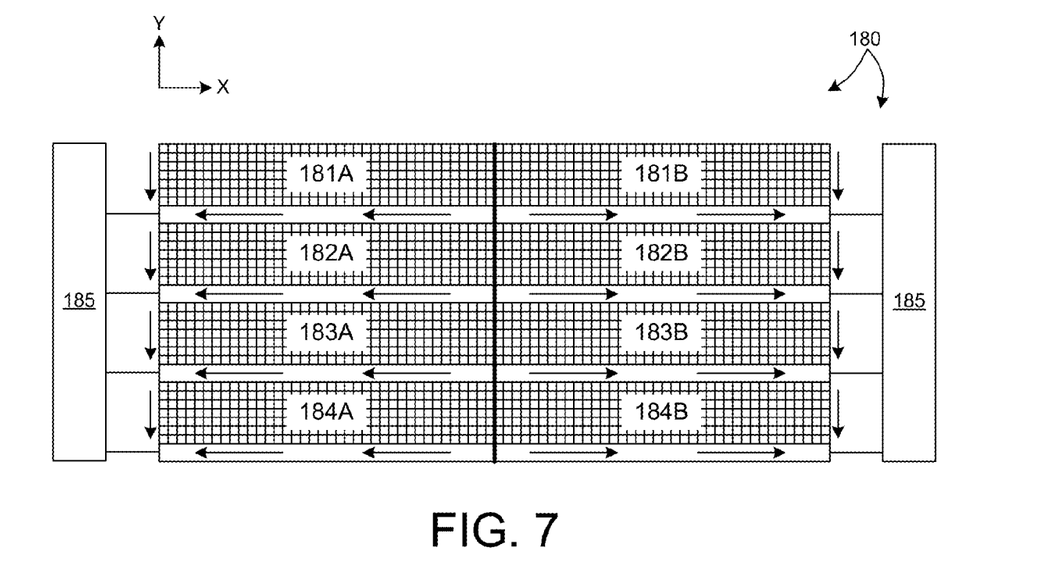
FIG. 7 is a simplified diagram illustrative of another embodiment 180 of detector 105 described with reference to metrology system 100.

FIG. 7 is a diagram illustrative of another embodiment 180 of detector 105 described with reference to FIGS. 1, 2 and 6. Detector 180 includes a multi-tap read out mode for each array of shift registers located in the photosensitive area. As depicted in FIG. 7, detector 180 is configured to direct the read-out of a portion of each photodetector array (e.g., portions of photodetector arrays 181A, 182A, 183A, and 184A) in one direction and the read-out of another portion of each photodetector array (e.g., portions of photodetector arrays 181B, 182B, 183B, and 184B) in the opposite direction to read-out electronics 185. In this manner, a multi-tap read-out approach may be applied to the detectors described in this patent document. Although two taps are described with reference to FIG. 7, any number of taps may be contemplated to increase horizontal read-out speed with a minimum of added complexity.

Figure 8:
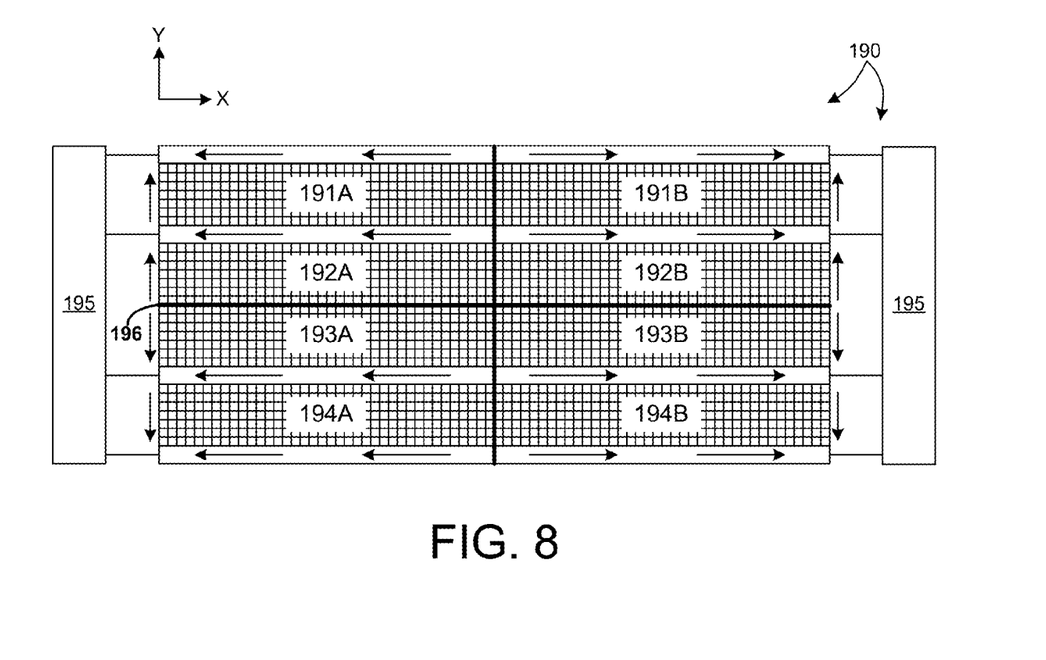
FIG. 8 is a simplified diagram illustrative of another embodiment 190 of detector 105 described with reference to metrology system 100.

FIG. 8 is a diagram illustrative of another embodiment 190 of detector 105 described with reference to FIGS. 1, 2, and 6. Detector 190 is configured with multiple taps to read-out electronics 195 as described with reference to FIG. 7. Detector 190 also includes a divider 196 across the photosensitive area that isolates arrays of photodetectors on one side of divider 196 from arrays of photodetectors on the opposite side of divider 196. As illustrated in FIG. 8, photodetector portions 191A, 192A, 191B, and 192B are isolated from photodetector portions 193A, 194A, 193B, and 194B by divider 196. By way of non-limiting example, divider 196 may be a row of dead photodetectors that effectively isolates arrays of photodetectors on opposite sides of the divider. As depicted in FIG. 8, the divider separates the direction of vertical charge transfer associated with shift registers on opposite sides of the divider. As illustrated in FIG. 8, charge stored in photodetectors above division 196 are vertically transferred upwards (in the positive y-direction), and charge stored in photodetectors below division 196 are vertically transferred downwards (in the negative y-direction). Division of photosensitive area by divider 196 provides a double width of photodetectors within the photosensitive area that is not subject to obfuscation due to the presence of an array of shift registers. In other words, the arrays of photodetectors adjacent to divider 196 are separated by divider 196, not an array of shift registers. Hence, in one example, it may be advantageous to focus the most common AOIs in this region to minimize signal contamination due to the presence of shift registers in the photosensitive area.

Although, detector 190 is illustrated in a multi-tap configuration, a divider may be implemented as part of detector in a single tap configuration in an analogous manner.

Figure 9:
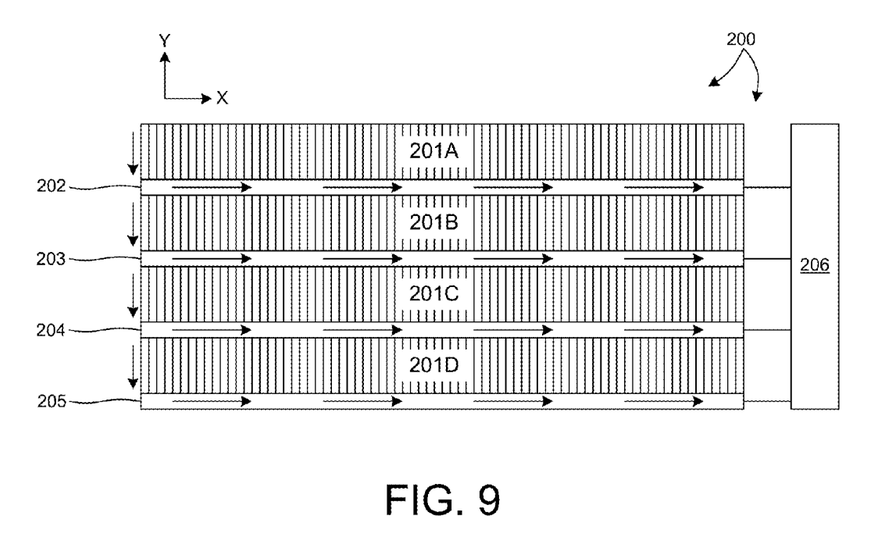
FIG. 9 is a simplified diagram illustrative of another embodiment 200 of detector 105 described with reference to metrology system 100.

FIG. 9 is a diagram illustrative of yet another embodiment 200 of detector 105 described with reference to FIGS. 1, 2, and 6. Detector 200 includes arrays of photodetectors 201A-201D having photodetector elements that are rectangular in shape. In the embodiment illustrated in FIG. 9, each array of photodetectors includes a single row of tall photodetectors with correspondingly deep wells, or associated wells to hold a sufficient amount of charge. An example of an array of photodetectors having associated wells is photodiode array model number S11151 manufactured by Hamamatsu, Photonics K.K. (Japan). In one example, a cross-section of an individual photodetector is 24 micrometers in the x-direction and 240 micrometers in the y-direction. In other words, each row of photodetector elements of detector 200 is the equivalent of 10 rows of photodetector elements at a pitch of 24 micrometers in the y-direction.

Charge transfer from an array of rectangularly shaped photodetectors to its associated shift-register (i.e., charge transfer in the y-direction as illustrated in FIG. 9) involves fewer clock cycles than an equivalent array of square shaped photodetectors. In the embodiment depicted in FIG. 9, each array of photodetectors includes a single row of photodetectors that may be read out to the associated array of shift registers in one clock cycle. In this manner, vertical binning is achieved physically by averaging light collected across each tall photodetector element.

Although each photodetector array illustrated in FIG. 9 includes a single row of "tall" photodetector elements, in general, each photodetector array may include any number of "tall" photodetector elements.

A metrology system, such as metrology system 100, that provides multiple AOI illumination onto the specimen and simultaneous collection of AOI regions onto a single detector without moving the illumination and collection paths may provide better measurement repeatability and stability due to fixed illumination and collection pupils and fixed illumination and collection field stops. In addition, systems with fixed imaging path optics and simultaneous acquisition of multiple AOIs have a throughput advantage over systems that achieve AOI resolution by moving imaging optics and/or sequential acquisition.

Moreover, a system such as metrology system 100 that subdivides the system NA into different AOI slices in the detection plane, rather than before the detection plane has a spot-size advantage.

Furthermore, a system such as metrology system 100 that simultaneously collects light associated with different AOI regions onto a single detector avoids additional wafer exposure that is required by systems that repeatedly illuminate the wafer with multiple AOIs and then sequentially select and collect light associated with each individual AOI after interaction with the wafer.

Metrology system 100 also includes a computing system 130 configured to control any of the components of metrology system 100. For example, computing system 130 is configured to select wavelengths of one or more illumination sources 121, angular frequency, azimuth angles, timing of a polarizer, illumination compensator, analyzer, collection compensator, etc.

Metrology system 100 also includes a computing system 130 employed to acquire signals 115 generated by optical detector 105 and determine properties of the specimen based at least in part on the acquired signals. As illustrated in FIG. 1, computing system 130 is communicatively coupled to optical detector 105. As described hereinbefore, detector 105 simultaneously detects light associated with multiple AOIs. The detected AOIs may be subsequently analyzed separately, or in parallel by computing system 130.

In some embodiments, detected light is converted into digital data corresponding to different AOIs and wavelengths. This data is independently analyzed as a function of AOI and wavelength. The data corresponding to the detected light may be divided so as to correspond to separate regions of the detector corresponding to different AOIs and wavelengths, and such separated data can then be analyzed as a function of AOI and wavelength. Certain embodiments allow improved measurement throughput by simultaneously analyzing light signals from different AOIs. An increased illumination NA allows the target size to be reduced by decreasing the diffraction limited spot size on the target region of the specimen. Alternatively, for a target whose size has not been reduced, the increased NA increases the ratio of detected light coming from within the target area to detected light coming from the surrounding area, reducing signal contamination.

In one example, optical detector 105 is an optical spectrometer and measurement data 115 includes an indication of the measured spectral response of the specimen based on one or more sampling processes implemented by an optical spectrometer.

In a further embodiment, computing system 130 is configured to access model parameters in real-time, employing Real Time Critical Dimensioning (RTCD), or it may access libraries of pre-computed models, or it may employ an algorithm that combines models computed in real-time with models from a library, for determining a value of at least one specimen parameter value associated with the specimen 101. In general, some form of CD-engine may be used to evaluate the difference between assigned CD parameters of a specimen and CD parameters associated with the measured specimen. Exemplary methods and systems for computing specimen parameter values are described in U.S. Pat. No. 7,826,071, issued on Nov. 2, 2010, to KLA-Tencor Corp., the entirety of which is incorporated herein by reference. In general, measurement models associated with not just CD, but also thin film and composition measurements may be applied by computing system 130 to resolve specimen parameter values.

As illustrated in FIG. 1, metrology tool 100 includes a specimen positioning system 110 configured to move specimen 101 under illumination beam 123. Computing system 130 communicates command signals to motion controller 114 of specimen positioning system 110 that indicate the desired position of specimen 101. In response, motion controller 114 generates command signals to the various actuators of specimen positioning system 110 to achieve the desired positioning of specimen 101.

In the embodiment depicted in FIG. 1, specimen positioning system 110 includes a wafer chuck 113, motion controller 114, a rotation stage 111 and a translation stage 112. Specimen 101 is supported on wafer chuck 113. Typically, specimen 101 is located with its geometric center approximately aligned the axis of rotation of rotation stage 111. In this manner, rotation stage 111 spins specimen 101 about its geometric center at a specified angular velocity, $\omega$, within an acceptable tolerance. In addition, translation stage 112 translates the specimen 101 in a direction approximately perpendicular to the axis of rotation of rotation stage 111 at a specified velocity, $V_T$. Motion controller 114 coordinates the spinning of specimen 101 by rotation stage 111 and the translation of specimen 101 by translation stage 112 to achieve the desired scanning motion of specimen 101 within system 100.

It should be recognized that the various steps described throughout the present disclosure may be carried out by a single computer system 130 or, alternatively, a multiple computer system 130. Moreover, different subsystems of the system 100, such as the specimen positioning system 110, may include a computer system suitable for carrying out at least a portion of the steps described herein. Therefore, the aforementioned description should not be interpreted as a limitation on the present invention but merely an illustration. Further, the one or more computing systems 130 may be configured to perform any other step(s) of any of the method embodiments described herein.

In addition, the computer system 130 may be communicatively coupled to the optical detector 105 and the optical illumination system 120 in any manner known in the art. For example, the one or more computing systems 130 may be coupled to computing systems associated with the optical detector 105 and the optical illumination system 120. In another example, any of the optical detector 105 and the optical illumination system 120 may be controlled directly by a single computer system coupled to computer system 130.

The computer system 130 of metrology system 100 may be configured to receive and/or acquire data or information from the subsystems of the system (e.g., optical detector 105, optical illumination system 120, and the like) by a transmission medium that may include wireline and/or wireless portions.

In this manner, the transmission medium may serve as a data link between the computer system 130 and other subsystems of the system 100.

Computer system 130 of the metrology system 100 may be configured to receive and/or acquire data or information (e.g., measurement results, modeling inputs, modeling results, etc.) from other systems by a transmission medium that may include wireline and/or wireless portions. In this manner, the transmission medium may serve as a data link between the computer system 130 and other systems (e.g., memory on-board metrology system 100, external memory, or external systems). For example, the computing system 130 may be configured to receive measurement data (e.g., signals 115) from a storage medium (i.e., memory 132 or an external memory) via a data link. For instance, spectral results obtained using a spectrometer of optical detector 105 may be stored in a permanent or semi-permanent memory device (e.g., memory 132 or an external memory). In this regard, the spectral results may be imported from on-board memory or from an external memory system. Moreover, the computer system 130 may send data to other systems via a transmission medium.

Computing system 130 may include, but is not limited to, a personal computer system, mainframe computer system, workstation, image computer, parallel processor, or any other device known in the art. In general, the term "computing system" may be broadly defined to encompass any device having one or more processors, which execute instructions from a memory medium.

Program instructions 134 implementing methods such as those described herein may be transmitted over a transmission medium such as a wire, cable, or wireless transmission link. For example, as illustrated in FIG. 1, program instructions stored in memory 132 are transmitted to processor 131 over bus 133. Program instructions 134 are stored in a computer readable medium (e.g., memory 132). Exemplary computer-readable media include read-only memory, a random access memory, a magnetic or optical disk, or a magnetic tape.

In one further aspect, metrology system 100 may include more than one detector, such as detector 105 described herein. One detector may be configured to detect light having wavelength and AOI dispersion in two directions as described hereinbefore and another detector may be similarly configured to detect light having wavelength and azimuth angle dispersion in two directions. In one embodiment, collection optics 103 is configured to simultaneously collect light from specimen 101 at multiple AOI and azimuth angles over a range of wavelengths. The collected light is directed to a beam splitter (not shown). The beam splitter directs a portion of the collected light to wavelength and AOI dispersing optics 104 and another portion of the collected light to wavelength and azimuth angle dispersing optics (not shown). Wavelength and AOI dispersing optics 104 disperse the wavelength and AOI properties of the incoming light in two different directions in the plane of detector 105 as described hereinbefore. Similarly, the wavelength and azimuth angle dispersing optics are configured to disperse the wavelength and azimuth angle properties of the light in two different directions in the plane of another detector configured in a manner described herein. The detector receives the dispersed light and simultaneously detects spatially separated regions of wavelength and azimuth angle properties of the collected light. In this manner, a metrology system may be configured to simultaneously detect three or more optical properties simultaneously by employing more than one detector configured as described herein.

Figure 10:
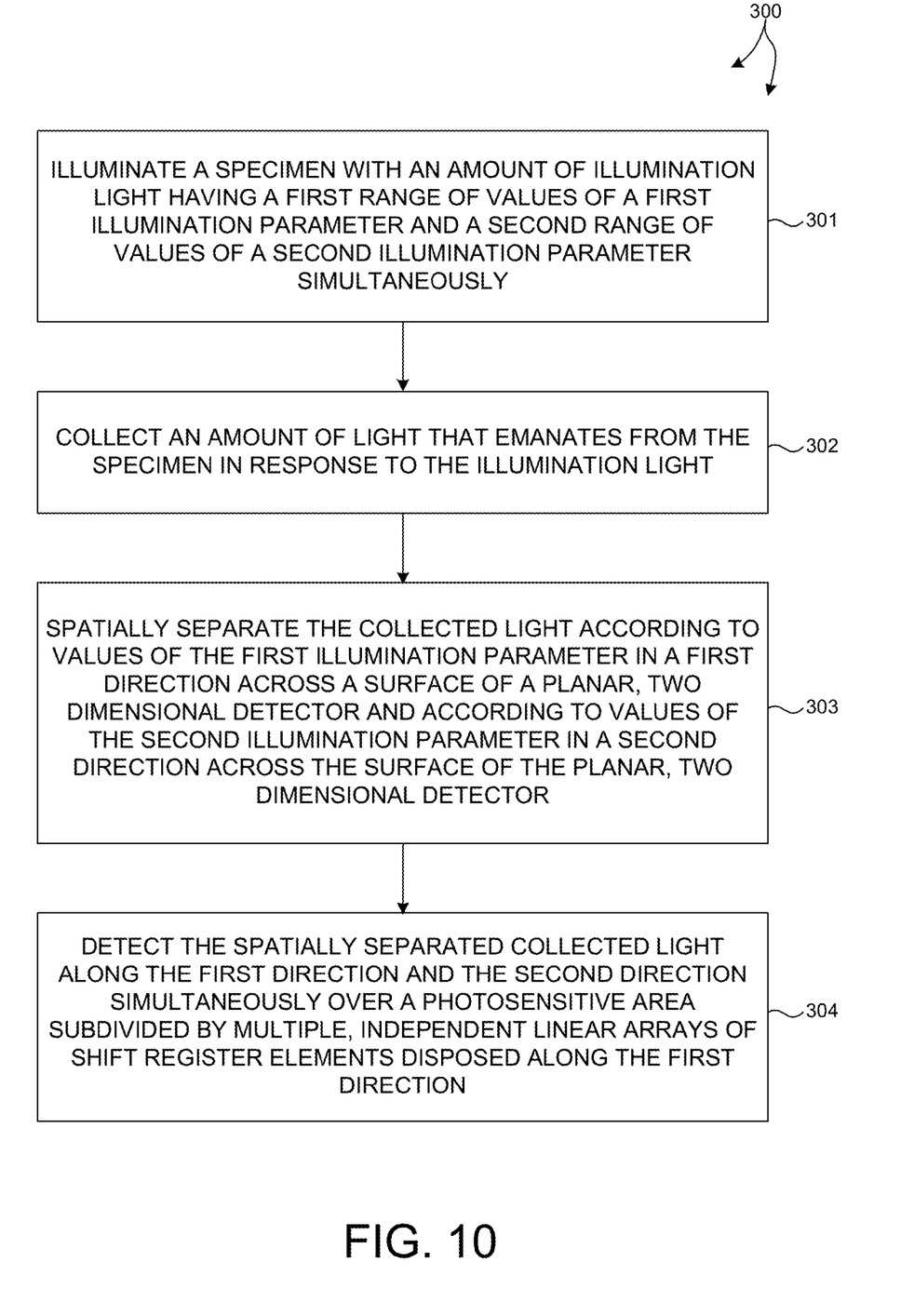
FIG. 10 illustrates a flowchart of an exemplary method 300 useful for enhancing the throughput of metrology systems that simultaneously illuminate a specimen with illumination light over a range of two or more illumination parameters.

FIG. 10 illustrates a flowchart of an exemplary method 300 useful for enhancing the throughput of metrology systems that simultaneously illuminate a specimen with illumination light over a range of two or more illumination parameters. In one non-limiting example, metrology system 100, described with reference to FIG. 1 is configured to implement method 300. In one aspect, it is recognized that data processing blocks of method 100 may be carried out via a pre-programmed algorithm executed by one or more processors of computing system 130. However, in general, the implementation of method 300 is not limited by the specific embodiments described herein.

In block 301, a specimen is illuminated with an amount of illumination light having a first range of values of a first illumination parameter and a second range of values of a second illumination parameter simultaneously.

In block 302, an amount of light is collected that emanates from the specimen in response to the illumination light.

In block 303, the collected light is spatially separated according to values of the first illumination parameter in a first direction across a surface of a planar, two dimensional detector and according to values of the second illumination parameter in a second direction across the surface of the planar, two dimensional detector.

In block 304, the spatially separated, collected light is detected along the first direction and the second direction simultaneously over a photosensitive area subdivided by multiple, independent linear arrays of shift register elements disposed along the first direction.

In some embodiments, the pixel structure of the array is designed to maximize collection efficiency over a range of radiation wavelengths (e.g., DUV and fluorescence signals). In this manner, the array is sensitive to all radiation wavelengths within a prescribed range.

Although, the aforementioned detection schemes have been described with reference to an individual illumination spot, the methods and systems described herein may also be applied analogously to a multi-spot system. In a multi-spot system, a number of illumination spots are employed simultaneously. Illumination light is supplied to these illumination spots from one or more illumination sources. Detectors, such as those described herein, may be selectively placed in the collection path of light reflected/scattered from any of the multiple illumination spots.

In many examples, the primary focus is to improve the throughput of metrology systems using multiple angles of incidence. These include but are not limited to multiple-AOI spectroscopic ellipsometry (SE) in its standard or Mueller matrix (MMSE) implementations, multiple-AOI spectroscopic reflectometry, beam profile reflectometry (BPR), or beam profile ellipsometry (BPE), with BPR or BPE technologies used in either one-dimensional or two-dimensional angle-resolved implementations.

However, in general the detector apparatus and methods described herein are compatible with all known optical metrology tools individually, or in combination as part of a combined measurement analysis. Such optical metrology tools include, by way of non-limiting example, spectroscopic ellipsometers, spectroscopic reflectometers, angle-resolved reflectometers and ellipsometers, spectroscopic scatterometry, scatterometry overlay, beam profile reflectometry, (angle and polarization resolved), beam profile ellipsometry, single or multiple discrete wavelength ellipsometry, multiple angle of incidence ellipsometry, and spectroscopic polarimetry.

In some examples, a metrology system employs two or more measurement technologies simultaneously, or sequentially. In one example, a co-located measurement system includes a broad-band ellipsometer and a broad-band reflectometer. In one aspect, a dispersed spectrum of light from the ellipsometer is directed to a group of one or more arrays of photodetectors and associated linear array(s) of shift registers of a detector as described herein. Furthermore, a dispersed spectrum of light from the reflectometer is directed to another group of one or more arrays of photodetectors and associated linear array(s) of shift registers of the same detector. As such, one or more optical properties associated with each measurement technology may be resolved by the same detector. The ellipsometer and the reflectometer may, or may not share the same spectrometer path. Data from both systems may, or may not be collected at the same time. Data from both systems may, or may not be collected from the same location on the wafer.

Various embodiments are described herein for an inspection system or tool that may be used for inspecting a specimen. The term "specimen" is used herein to refer to a wafer, a reticle, or any other sample that may be inspected for defects, features, or other information (e.g., an amount of haze or film properties) known in the art.

As used herein, the term "wafer" generally refers to substrates formed of a semiconductor or non-semiconductor material. Examples include, but are not limited to, monocrystalline silicon, gallium arsenide, and indium phosphide. Such substrates may be commonly found and/or processed in semiconductor fabrication facilities. In some cases, a wafer may include only the substrate (i.e., bare wafer). Alternatively, a wafer may include one or more layers of different materials formed upon a substrate. One or more layers formed on a wafer may be "patterned" or "unpatterned." For example, a wafer may include a plurality of dies having repeatable pattern features.

A "reticle" may be a reticle at any stage of a reticle fabrication process, or a completed reticle that may or may not be released for use in a semiconductor fabrication facility. A reticle, or a "mask," is generally defined as a substantially transparent substrate having substantially opaque regions formed thereon and configured in a pattern. The substrate may include, for example, a glass material such as quartz. A reticle may be disposed above a resist-covered wafer during an exposure step of a lithography process such that the pattern on the reticle may be transferred to the resist.

In one or more exemplary embodiments, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a general purpose or special purpose computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media.

Although certain specific embodiments are described above for instructional purposes, the teachings of this patent document have general applicability and are not limited to the specific embodiments described above. In one example, inspection system 100 may include more than one light source (not shown). The light sources may be configured differently or the same. For example, the light sources may be configured to generate light having different characteristics that can be directed to a wafer at the same or different illumination areas at the same or different angles of incidence at the same or different times. The light sources may be configured according to any of the embodiments described herein. In addition one of the light sources may be configured according to any of the embodiments described herein, and another light source may be any other light source known in the art. In some embodiments, an inspection system may illuminate the wafer over more than one illumination area simultaneously. The multiple illumination areas may spatially overlap. The multiple illumination areas may be spatially distinct. In some embodiments, an inspection system may illuminate the wafer over more than one illumination area at different times. The different illumination areas may temporally overlap (i.e., simultaneously illuminated over some period of time). The different illumination areas may be temporally distinct. In general, the number of illumination areas may be arbitrary, and each illumination area may be of equal or different size, orientation, and angle of incidence. In yet another example, inspection system 100 may be a scanning spot system with one or more illumination areas that scan independently from any motion of wafer 123. In some embodiments an illumination area is made to scan in a repeated pattern along a scan line. The scan line may or may not align with the scan motion of wafer 123. Although as presented herein, wafer positioning system 125 generates motion of wafer 123 by coordinated rotational and translational movements, in yet another example, wafer positioning system 100 may generate motion of wafer 123 by coordinating two translational movements. For example motion wafer positioning system 125 may generate motion along two orthogonal, linear axes (e.g., X-Y motion). In such embodiments, scan pitch may be defined as a distance between adjacent translational scans along either motion axis. In such embodiments, an inspection system includes an illumination source and a wafer positioning system. The illumination source supplies an amount of radiation to a surface of a wafer over an illumination area. The wafer positioning system moves the wafer in a scanning motion characterized by a scan pitch (e.g., scanning back and forth in one direction and stepping by an amount equal to the scan pitch in the orthogonal direction).

Accordingly, various modifications, adaptations, and combinations of various features of the described embodiments can be practiced without departing from the scope of the invention as set forth in the claims.

What is claimed is:

1. An optical detector comprising:
  a photosensitive area having a first dimension in a first direction and a second dimension in a second direction, the first direction orthogonal to the second direction, the first dimension greater than the second dimension, the photosensitive area including:
a first array of photodetectors arranged in a first portion of the photosensitive area along the first direction;
a second array of photodetectors arranged in a second portion of the photosensitive area along the first direction; and
a first linear array of shift register elements disposed along the first direction between the first and the second array of photosensitive elements, wherein a charge accumulated on the first array of photodetectors is transferred to the first linear array of shift register elements, and wherein a charge accumulated on the second array of photodetectors is transferred to the a second linear array of photodetector elements.

2. The optical detector of claim 1, further comprising:
a third array of photodetectors arranged in a third portion of the photosensitive area along the first direction, wherein the third array of photodetectors is disposed adjacent to the first array of photodetectors.

3. The optical detector of claim 1, wherein a first portion of the charge transferred to the first linear array of shift register elements is read out in a first direction and a second portion of the charge transferred to the first linear array of shift register elements is read out in a second direction opposite the first direction.

4. The optical detector of claim 1, wherein each of the photodetectors of the first array of photodetectors are read out sequentially.

5. The optical detector of claim 1, wherein the first array of photodetectors is two dimensional including a plurality of rows of photodetector elements aligned with the first direction and a plurality of columns of photodetector elements aligned with the second direction, wherein the plurality of rows of the first array of photodetectors are read out in parallel.

6. The optical detector of claim 1, wherein the first array of photodetectors is a linear array of rectangularly shaped photodetector elements aligned with the first direction.

7. The optical detector of claim 1, further comprising:
a mechanical shield disposed over the first and second arrays of photodetectors in an optical path of incoming light.

8. The optical detector of claim 1, wherein each of the photodetectors is a charge coupled device or a photodiode.

9. The optical detector of claim 1, wherein the first array of photodetectors is two dimensional including a first plurality of rows of photodetector elements aligned with the first direction and a second plurality of columns of photodetector elements aligned with the second direction, wherein the second plurality of columns is at least ten times greater than the first plurality of rows.

10. An optical metrology system comprising:
an illumination subsystem including an illumination source and illumination optics configured to simultaneously illuminate a specimen with an amount of illumination light having a first range of values of a first illumination parameter and a second range of values of a second illumination parameter;
a collection optics subsystem configured to collect an amount of light that emanates from the specimen in response to the illumination light;
a dispersing optics subsystem configured to spatially separate the collected light according to values of the first illumination parameter in a first direction, spatially separate the collected light according to values of the second illumination parameter in a second direction, and project the spatially separated collected light onto a planar, two dimensional detector surface;
a planar, two dimensional detector configured to receive the spatially separated collected light onto the planar, two dimensional detector surface and detect the spatially separated collected light along the first direction and the second direction simultaneously, the planar, two dimensional detector having a photosensitive area including:
a first array of photodetectors arranged in a first portion of the photosensitive area along the first direction;
a second array of photodetectors arranged in a second portion of the photosensitive area along the first direction; and
a first linear array of shift register elements disposed along the first direction between the first and the second array of photosensitive elements, wherein a charge accumulated on the first array of photodetectors is transferred to the first linear array of shift register elements, and wherein a charge accumulated on the second array of photodetectors is transferred to the a second linear array of photodetector elements.

11. The optical metrology system of claim 10, wherein each of the photodetectors of the first array of photodetectors are read out sequentially.

12. The optical metrology system of claim 10, wherein the first array of photodetectors is two dimensional including a plurality of rows of photodetector elements aligned with the first direction and a plurality of columns of photodetector elements aligned with the second direction, wherein the plurality of rows of the first array of photodetectors are read out in parallel.

13. The optical detector of claim 10, wherein the first array of photodetectors is a linear array of rectangularly shaped photodetector elements aligned with the first direction.

14. The optical metrology system of claim 10, further comprising:
a mechanical shield disposed over the first and second arrays of photodetectors in an optical path of incoming light.

15. The optical metrology system of claim 10, further comprising:
an optical shuttering mechanism to cut off illumination of the photosensitive area of the planar, two dimensional detector by the illumination subsystem when the first and second arrays of photodetectors are read out.

16. The optical metrology system of claim 15, wherein the optical shuttering mechanism is a rotating chopper wheel disposed in an optical path of the collected light.

17. A method comprising:
illuminating a specimen with an amount of illumination light having a first range of values of a first illumination parameter and a second range of values of a second illumination parameter simultaneously;
collecting an amount of light that emanates from the specimen in response to the illumination light;
spatially separating the collected light according to values of the first illumination parameter in a first direction across a surface of a planar, two dimensional detector and according to values of the second illumination parameter in a second direction across the surface of the planar, two dimensional detector; and
detecting the spatially separated collected light along the first direction and the second direction simultaneously over a photosensitive area including:
a first array of photodetectors arranged in a first portion of the photosensitive area along the first direction;

a second array of photodetectors arranged in a second portion of the photosensitive area along the first direction; and a first linear array of shift register elements disposed along the first direction between the first and the second array of photosensitive elements, wherein a charge accumulated on the first array of photodetectors is transferred to the first linear array of shift register elements, and wherein a charge accumulated on the second array of photodetectors is transferred to the a second linear array of photodetector elements.

18. The method of claim 17, further comprising:

shielding the first linear array of shift register elements from the collected light.

19. The method of claim 17, further comprising:

shielding the first linear array of shift register elements from the collected light during read out of the first linear array of shift register elements.

20. The method of claim 17, further comprising:

reading out a plurality of rows of the first array of photodetectors in parallel, wherein the first array of photodetectors is two dimensional including the plurality of rows of photodetector elements aligned with the first direction and a plurality of columns of photodetector elements aligned with the second direction.

* * * * *